US012661167B2

(12) United States Patent
Lindvall et al.

(10) Patent No.: US 12,661,167 B2
(45) Date of Patent: Jun. 23, 2026

(54) SHEATH FOR PERCUTANEOUS CABLE INSERTION (SPCI)

(71) Applicant: SPCI, LLC, Tampa, FL (US)

(72) Inventors: Eric M. Lindvall, Clovis, CA (US); Marshall Simmons, Tampa, FL (US)

(73) Assignee: SPCI, LLC, Tampa, FL (US)

( * ) Notice: Subject to any disclaimer, the term of this patent is extended or adjusted under 35 U.S.C. 154(b) by 73 days.

(21) Appl. No.: 17/734,476

(22) Filed: May 2, 2022

(65) Prior Publication Data

US 2023/0346443 A1    Nov. 2, 2023

(51) Int. Cl.
*A61B 17/88* (2006.01)
*A61B 17/56* (2006.01)

(52) U.S. Cl.
CPC .... *A61B 17/8861* (2013.01); *A61B 2017/564* (2013.01)

(58) Field of Classification Search
CPC ........... A61B 17/8861; A61B 17/1697; A61B 2017/0445; A61B 2017/3449; Y10T 403/555; Y10T 403/5733; Y10T 403/51; Y10T 403/50; F16B 7/0426; F16B 2200/10
See application file for complete search history.

(56) References Cited

U.S. PATENT DOCUMENTS

| 5,476,465 | A | * | 12/1995 | Preissman | .............. | A61B 17/82 |
| | | | | | | 606/279 |
| 6,053,921 | A | * | 4/2000 | Wagner | .............. | A61B 17/8869 |
| | | | | | | 606/103 |
| 6,099,527 | A | * | 8/2000 | Hochschuler | .......... | A61B 17/82 |
| | | | | | | 606/279 |
| 2009/0198188 | A1 | * | 8/2009 | Mialhe | .............. | A61B 17/3462 |
| | | | | | | 604/167.03 |
| 2011/0071359 | A1 | * | 3/2011 | Bonadio | ............ | A61B 17/0293 |
| | | | | | | 600/184 |
| 2015/0335320 | A1 | * | 11/2015 | Keating | ............. | A61B 17/0469 |
| | | | | | | 606/144 |

* cited by examiner

*Primary Examiner* — Julianna N Harvey
(74) *Attorney, Agent, or Firm* — Schott, P.C.

(57) ABSTRACT

A cable passer sheath engages the end hole of a cable passer. The sheath includes an outer body having an outer diameter and having a cable passer engagement opening at a cable passer engagement end thereof and a cable engagement opening at a cable engagement end thereof. The cable passer engagement opening and cable engagement opening are connected by a passage through the outer body.

9 Claims, 11 Drawing Sheets

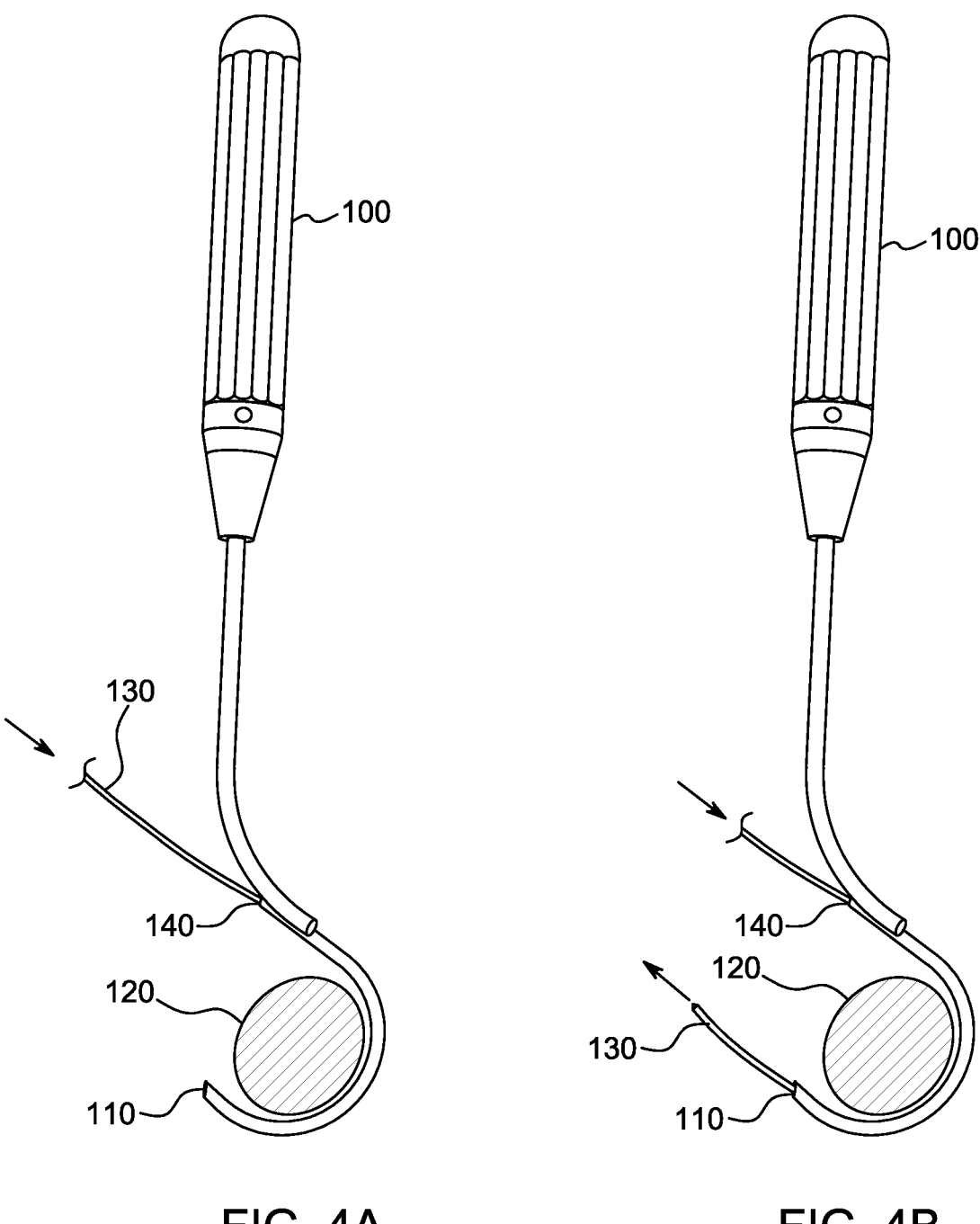
FIG. 4A                    FIG. 4B

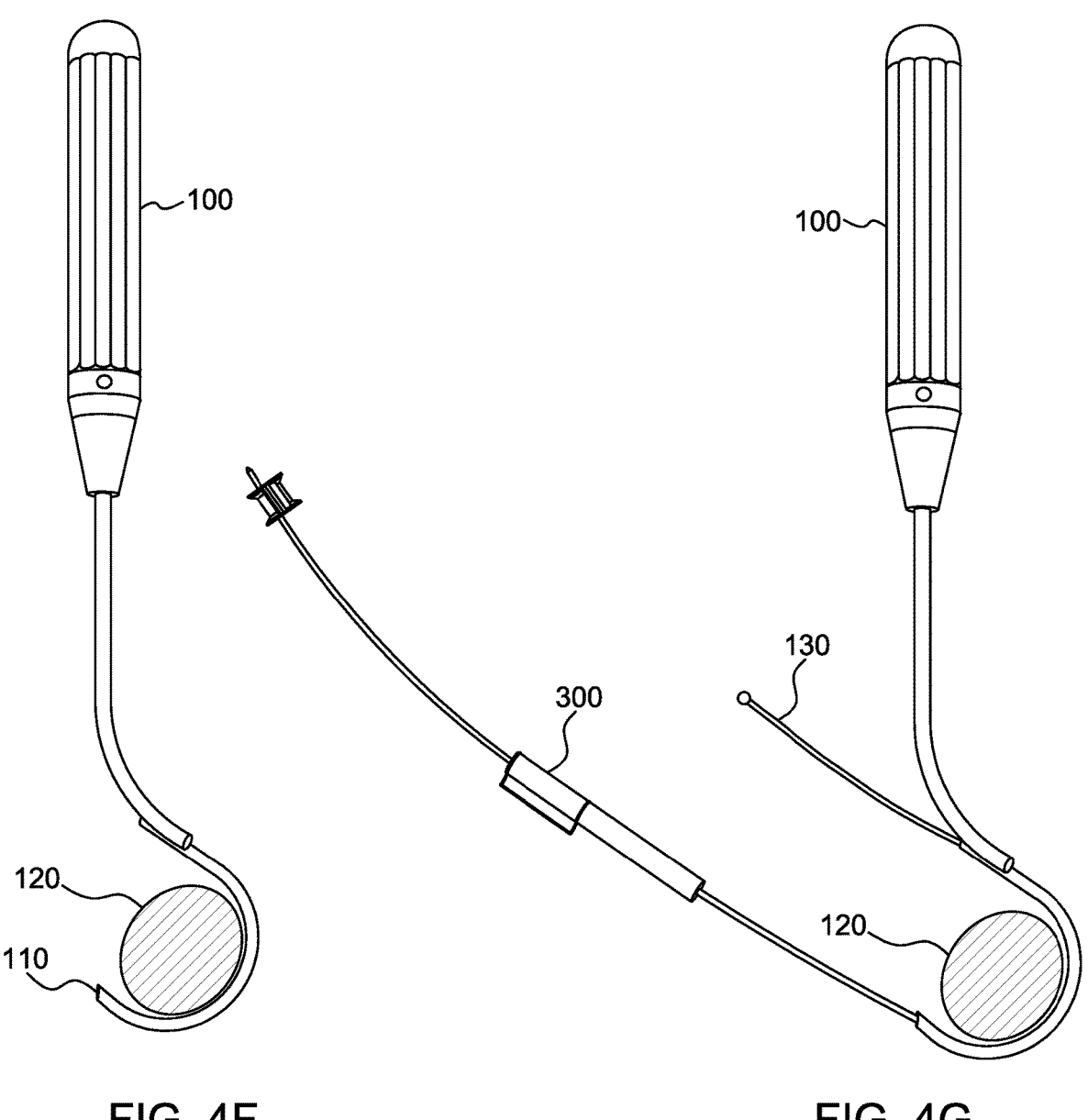
FIG. 4F                    FIG. 4G

SHEATH FOR PERCUTANEOUS CABLE INSERTION (SPCI)

BACKGROUND

Surgeons may use cerclage and tension band wiring techniques in orthopedic surgical procedures to repair fractures or other periprosthetic conditions requiring additional support. The following cerclage wiring configurations may be used: wrapped around once and wrapped around twice patterns locked with a symmetric twist, knot twist, eyelet bend-back, or crimped double barrel sleeve; doubled symmetric twist; hairpin loop; or Mittelmeier's double loop bend-back with twist. Other techniques may also be possible.

Any such techniques involve common steps. First surgeon selects an appropriately sized cable passer 100 as shown in FIG. 1, which size depends on the bone size 120 and access limitations. Ideally, the cable passer 100 selected by the surgeon for its open gap 150 size that partially encircles the bone 120 without damaging the bone 120 or other soft tissues.

The surgeon will create an access incision through soft tissue on either side of the bone 120 so the surgeon can locate the cable passer around the bone 120, such that the surgeon can access the end hole 110 and shaft hole 140 through the incision. The surgeon then threads a cable 130 into an end hole 110 of the cable passer 100 that the surgeon can access. The end hole 110 connects through an open passage in the cable passer 100 to shaft hole 140. With the cable 130 wrapped around the bone 120 to be secured, the surgeon can remove the cable passer 100.

After the surgeon positions the cable, they position a cable crimp, tension, the cable, crimp the cable, and cut the cable. This disclosure does not describe these steps in detail because the invention focuses on the placement of the cable 130 around the bone 120 using the cable passer 100.

One of the challenges in this procedure is that accessing the end hole 110 through the incision can be challenging. There is tissue interference while accessing the end hole and passing the cable 130 into the end hole may require a much larger incision than simply enough to accommodate passage of the cable 130.

Larger incisions invite more infection, slower healing, more scarring, and longer operation time, and greater blood loss. A solution to accessing the end hole 110 more easily would address some or all of these issues.

SUMMARY OF THE EMBODIMENTS

A cable passer sheath engages the end hole of a cable passer. The sheath includes an outer body having an outer diameter and having a cable passer engagement opening at a cable passer engagement end thereof and a cable engagement opening at a cable engagement end thereof. The cable passer engagement opening, and cable engagement opening are connected by a passage through the outer body.

BRIEF DESCRIPTION OF THE DRAWINGS

FIG. 3A B shows the cable passer sheath looking towards the cable passer end hole end into the cable passer sheath.

FIGS. 4A-4J show a series of steps for using the device in a surgical procedure.

DETAILED DESCRIPTION OF THE EMBODIMENTS

Method of Using the Sheath

Figure 1:
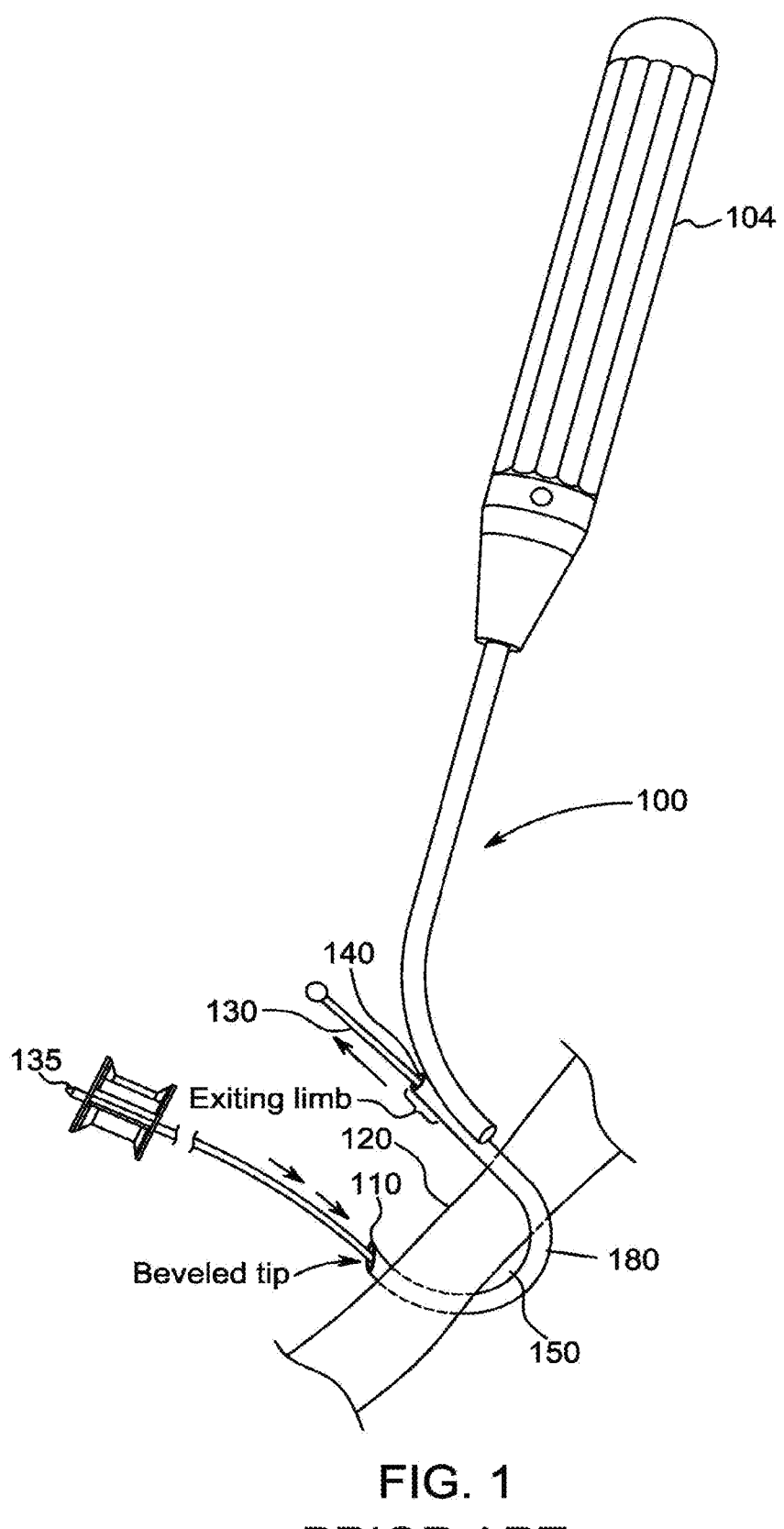
FIG. 1 shows a cable passer of the prior art engaged around a bone.

A surgeon may use the inventive passer sheath in a method of engaging a cable around a fractured bone using the following steps, and with reference to FIGS. 4A-4J.

First, the surgeon may make an incision through tissue near the break. The incision can be done using methods known to those or skill in the art but the incision would be large enough to accommodate the insertion of an end of the cable passer 100.

Then as shown in FIG. 4A, the surgeon positions the cable passer 100 around the bone 120 by leading an end hole end 114 of the cable passer 100 through the incision and locates the bone 120 within a cable passer passage gap 150, which is generally bounded by the "c" shape of an end of the cable passer 300 opposite the handle 104.

As shown in FIG. 4A, the surgeon passes a cable 130 through a shaft hole 140 of the cable passer 100, wherein the shaft hole 140 is in communication with the end hole 110 via a cable passer passage 170 through the "c" shaped portion 180 of the passer 100.

The surgeon then advances the cable 130 until it can be seen exiting end hole 110 as shown in FIG. 4B.

Figure 4C:
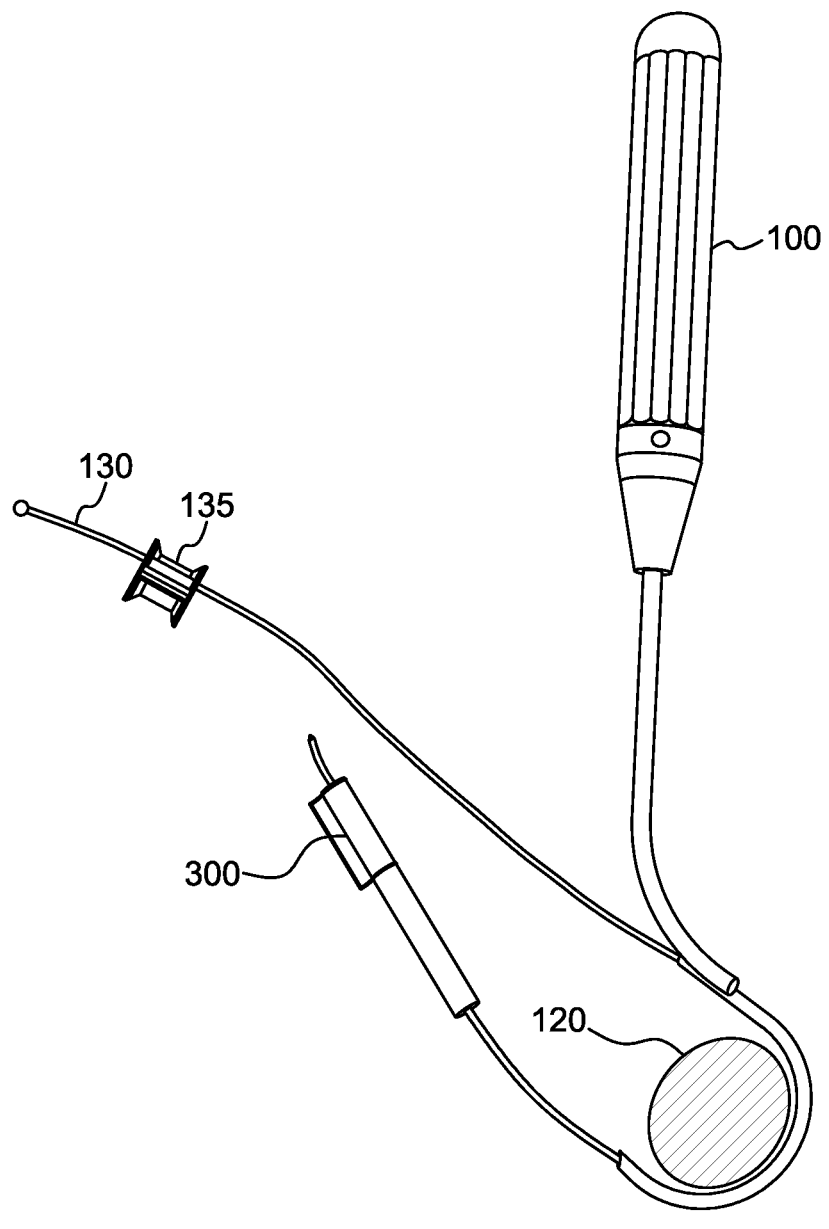

FIG. 4C shows the surgeon passing a cable passer sheath 300 in a cannulated fashion over the cable 130 exiting the end hole 110.

Figure 2:
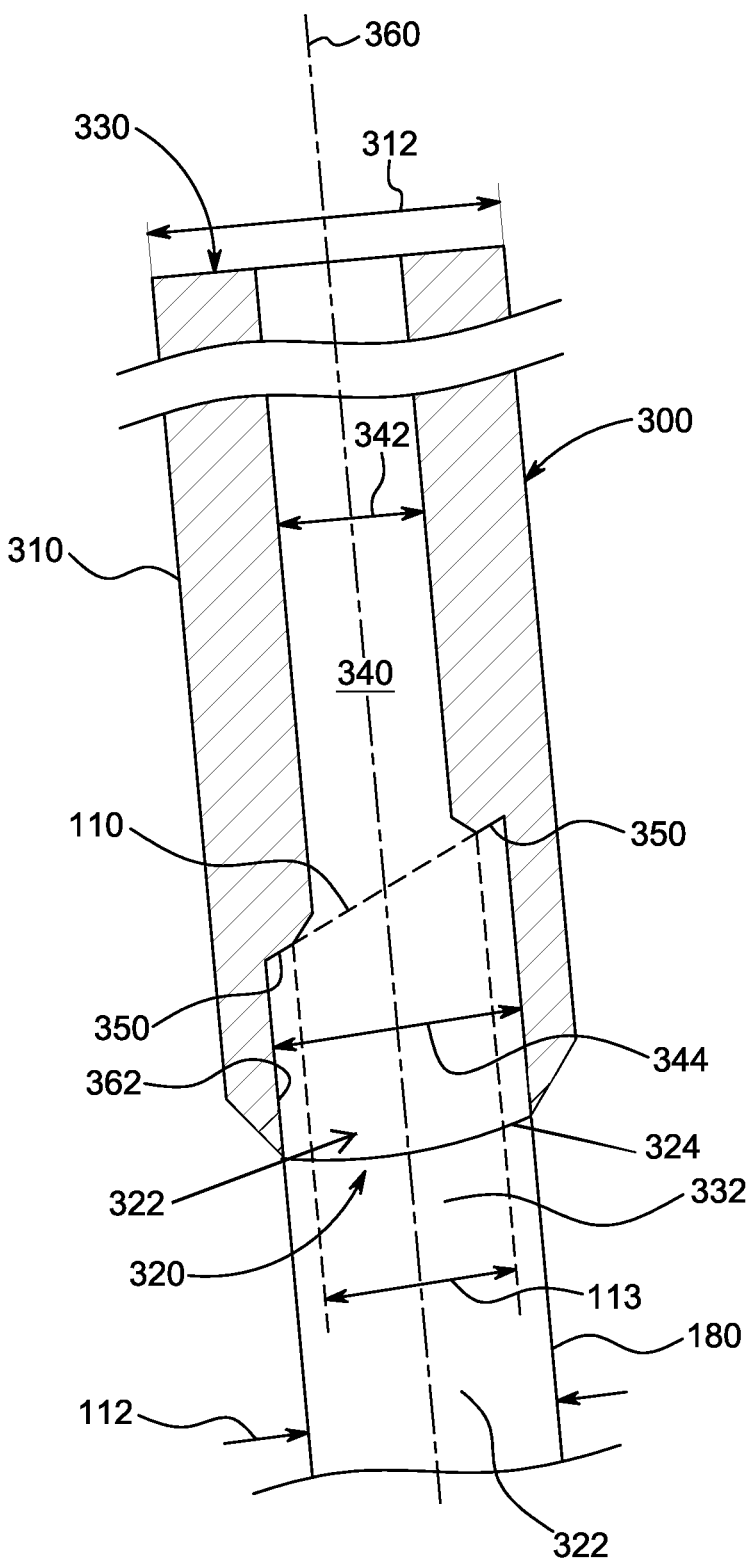
FIG. 2 shows a cross section through the cable passer sheath engaged to a cable passer end hole.
Figure 3A:
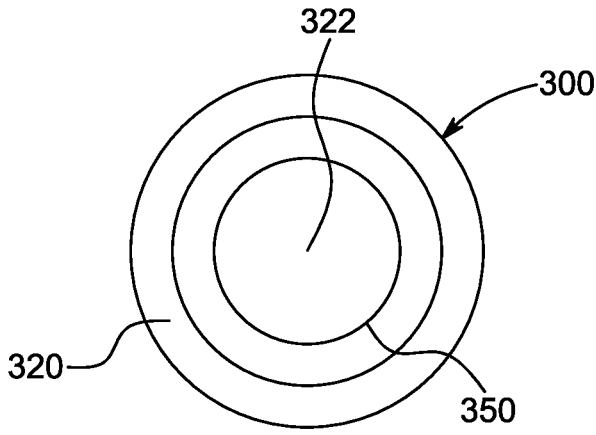
FIG. 3A shows the cable passer sheath looking from the cable passer end hole end into the cable passer sheath.
Figure 3B:
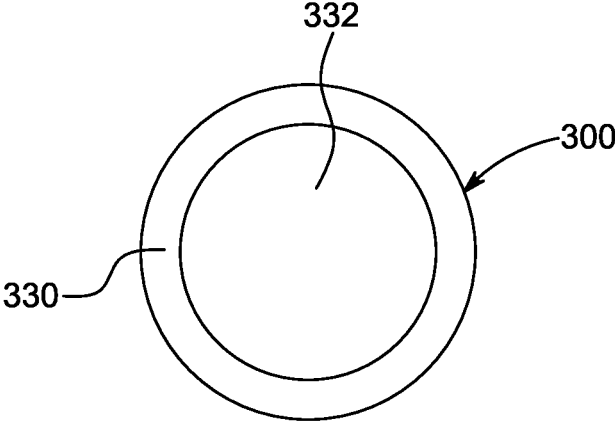
FIG. 3C shows the cable passer sheath in elevation.
FIG. 3D shows the cable passer sheath split open along its slit.
Figure 3C:
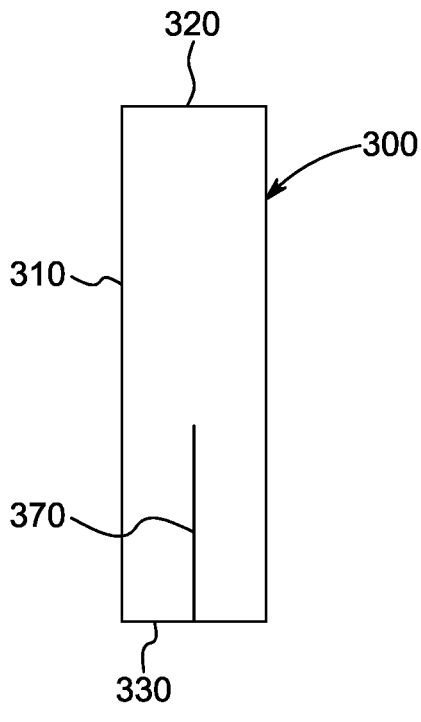
Figure 3D:
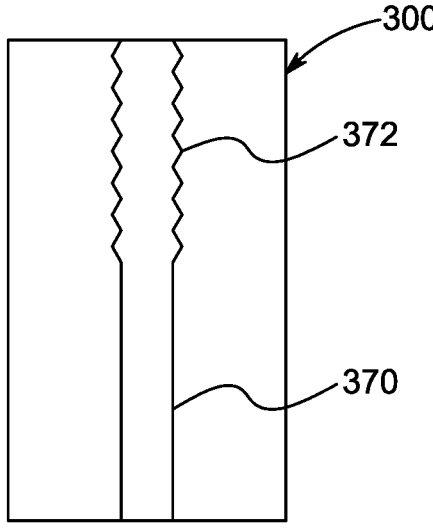
Figure 4D:
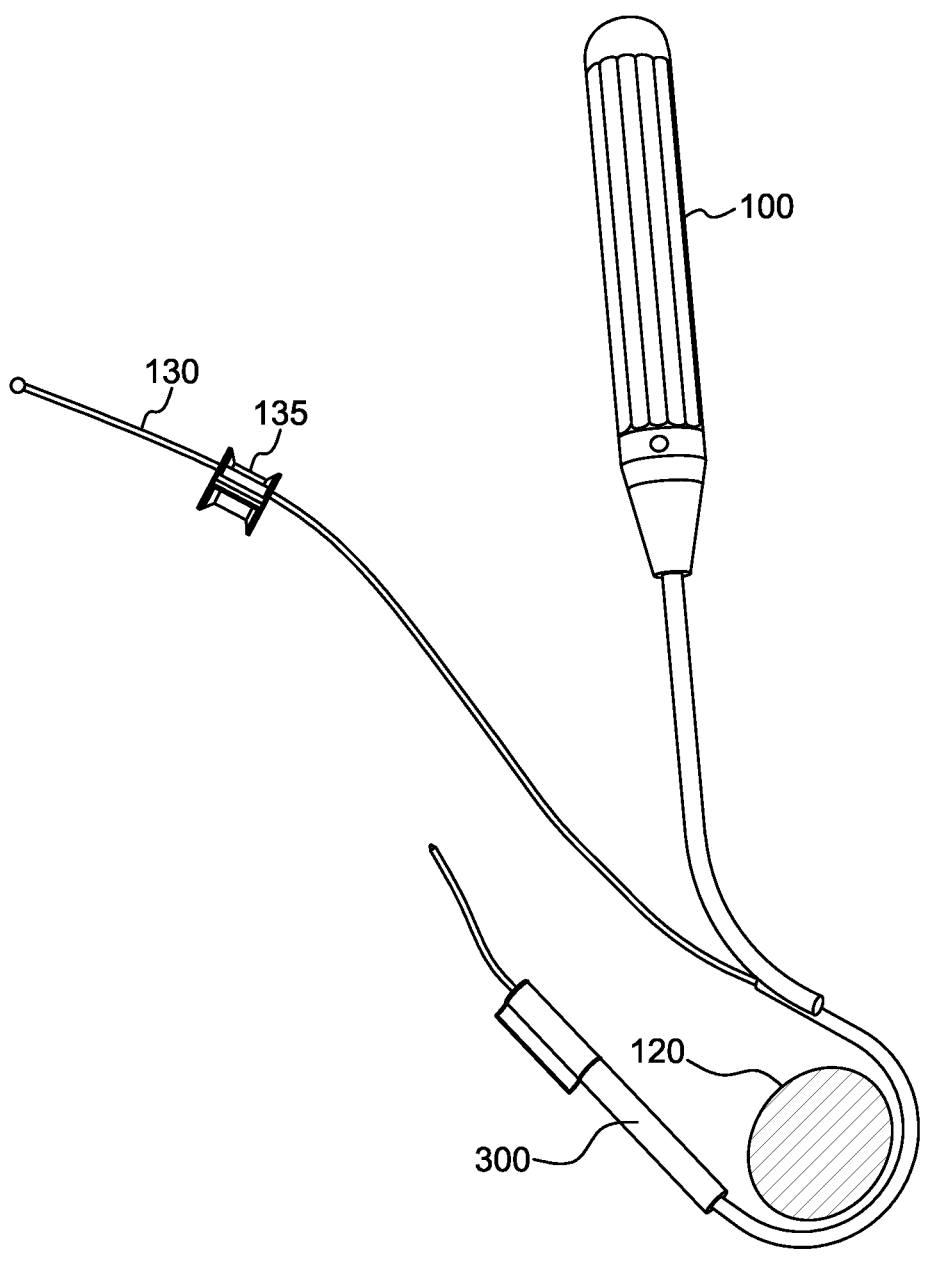
Figure 4E:
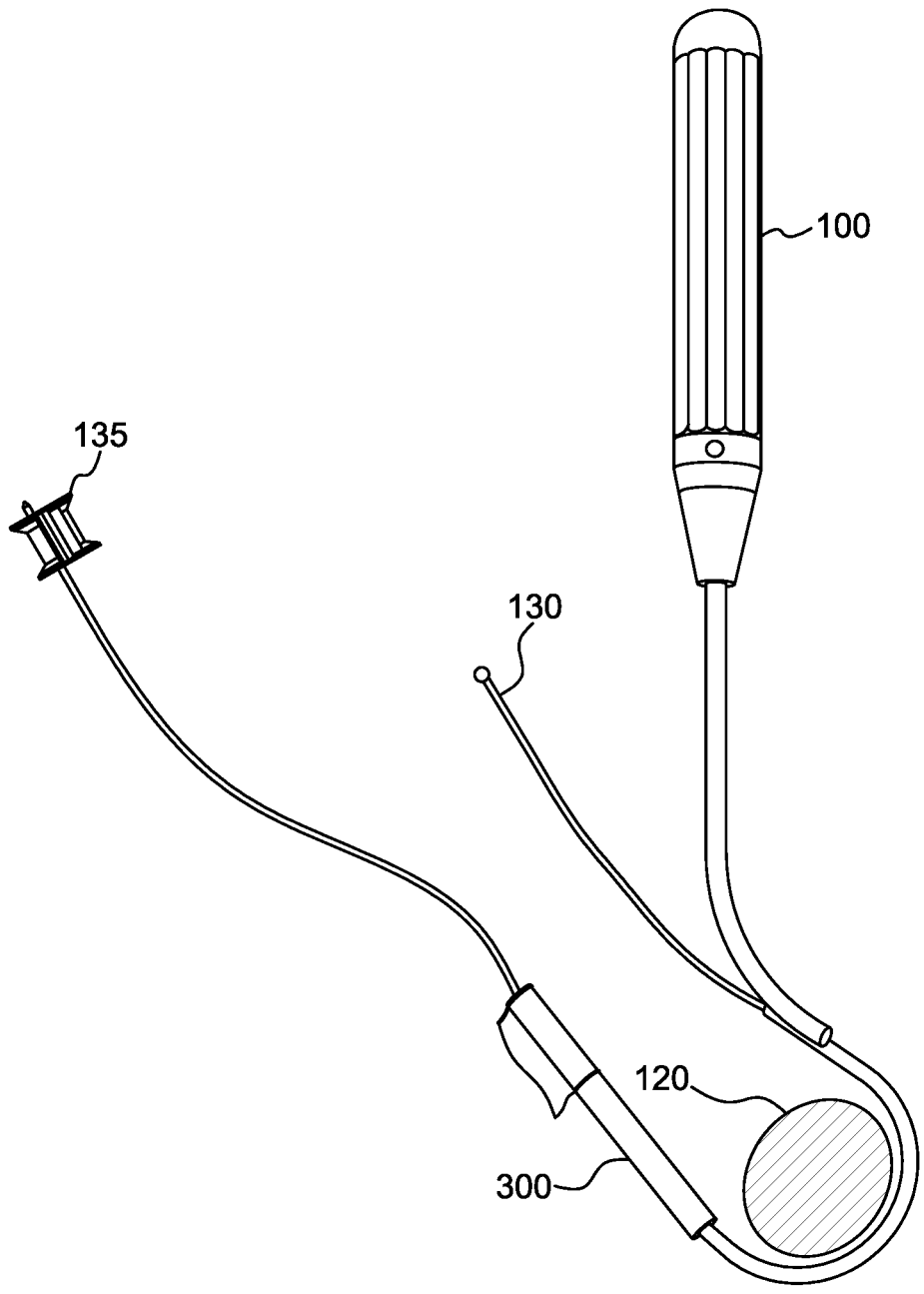

As shown in FIG. 4D and in cross sectional view in FIG. 2, the surgeon engages the cable passer sheath 100 to the cable passer end hole end 114 to its state shown in FIG. 4E.

At this point, the surgeon may, for reasons of convenience in the procedure and if the operating equipment permits, remove the cable passer sheath 300 and cable passer 100, and proceed to tighten the cable 130 Otherwise, for convenience and because tools already exist that work better with the cable passer 100 and cable 130 fed in a certain direction (the crimp devices for example), the surgeon may remove the cable 130 from the cable passer sheath 300 and cable passer passage 170 to the state shown in FIG. 4F. The surgeon then reinserts in the opposite direction (i.e. into sheath first and exit cable passer shaft hole 140). This may be performed because of the inability to remove the cable passer 100 in the initially described cable orientation due to an associated set screw or crimpable piece 135 having a diameter larger than the cable passer cannulation. In the event the cable 130 is passed in the currently described direction (end hole first 110 and exiting shaft hole 140), the sheath 300 then becomes an extension of the cable passer 100 making the insertion of the cable 130 into the cable passer 100 easier.

Further, the purpose for the sheath and passing the cable first in the "wrong" direction (through the shaft hole 140 first) is that the cable passer end hole 110 will not be visible (while the shaft hole 140 will remain visible). Making a very large incision, increasing blood loss allows visibility of the end hole and therefore passage of the cable in current technique.

By making a small incision, passing the cable in a retrograde fashion and having in present itself by protruding out of the wound (without visualizing the end hole 110), the sheath 300 can now be passed in a cannulated fashion over the cable and intussuscepting itself firmly onto the end hole 110. Now the cable can be removed and passed the correct direction without again having to visualize the end hole 110. It is the set screw or crimpable device/apparatus on the cable that also now blocks the removal of the sheath. Therefore, the sheath has a longitudinal slot that the cable can exit in order to avoid having to remove the sheath over the set screw apparatus. The material of the sheath will be slightly pliable to allow for slight opening of the slit in the sheath as the sheath is pulled away from the cable. This longitudinal slot will not technically be an open space as cable passage through the sheath should not allow for the cable to escape through the slit.

The surgeon may then pass the cable 130 back through the cable passer sheath 300, through the end hole 110, into the cable passer passage 170 and out the shaft hole 140, so that the cable (without engagement tools not shown) looks again like the state shown in FIG. 4E.

At this point, the surgeon may, for reasons of convenience in the procedure, remove the cable passer sheath 300 and cable passer 100, and proceed to tighten the cable 130 as described above. Otherwise, for convenience and because tools already exist that work better with the cable passer 100 and cable 130 fed in a certain direction, the surgeon may then remove the cable passer sheath 300 by disengaging the cable passer sheath 300 from the cable passer end hole end 114 as shown in FIG. 4G.

Figure 4H:
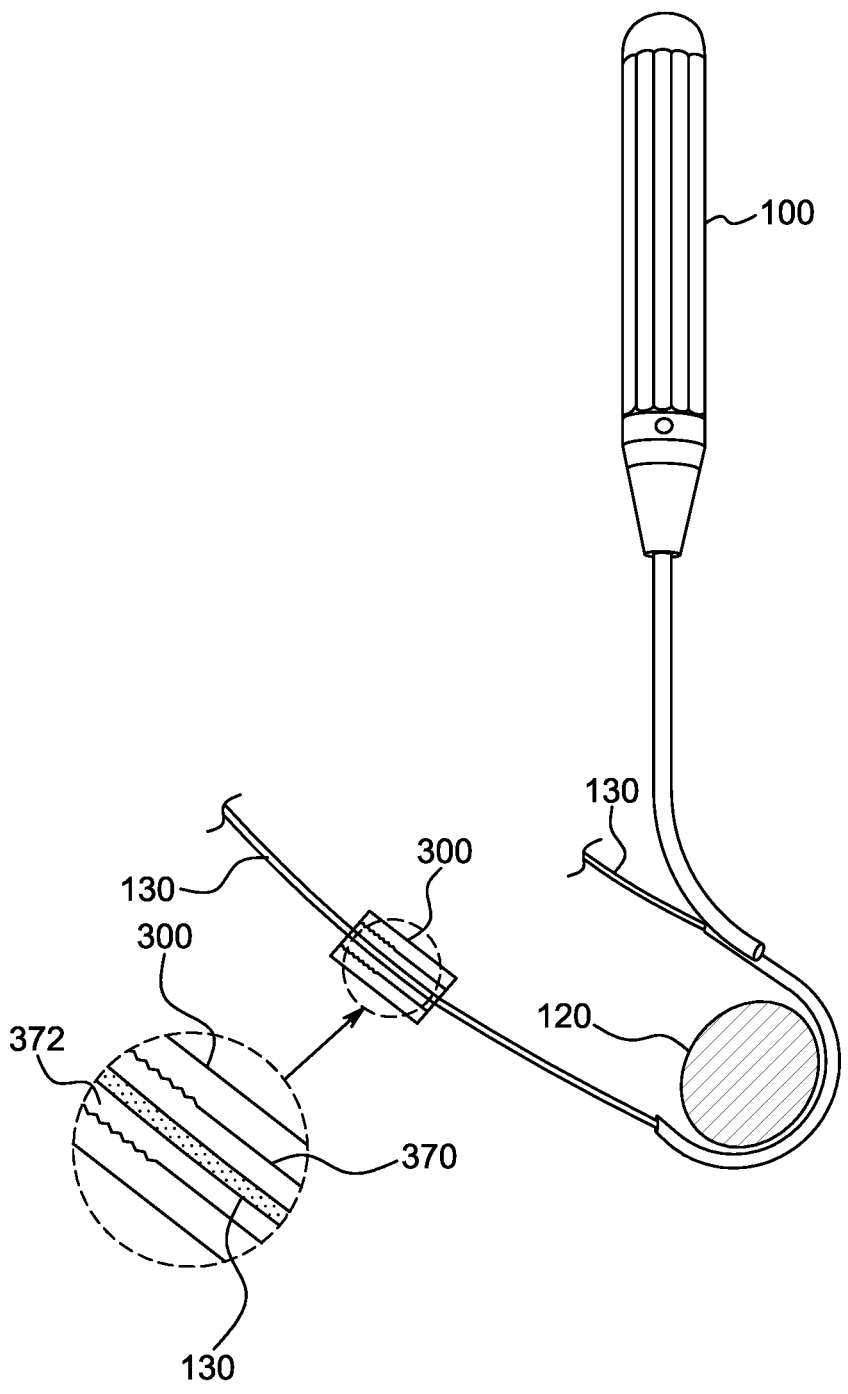
Figure 4I:
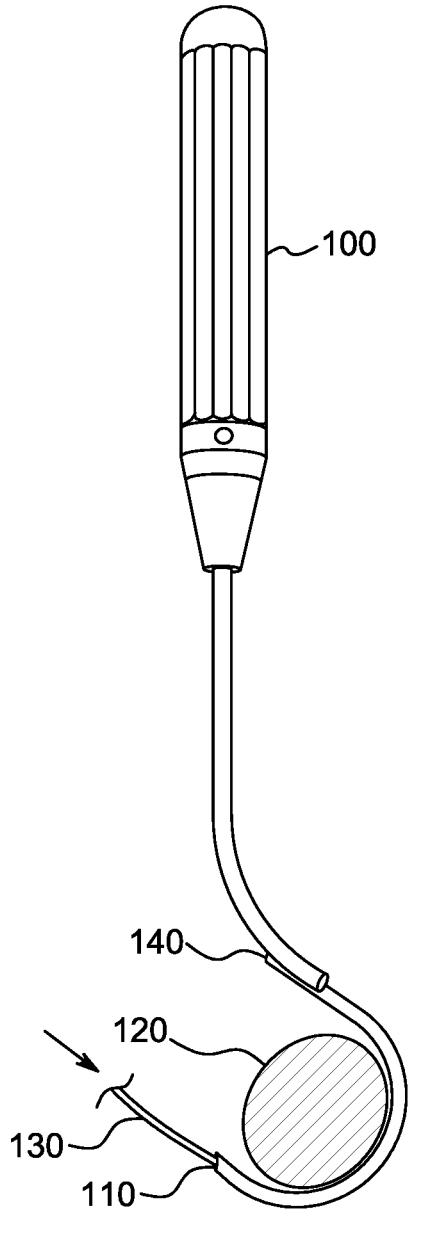
Figure 4J:
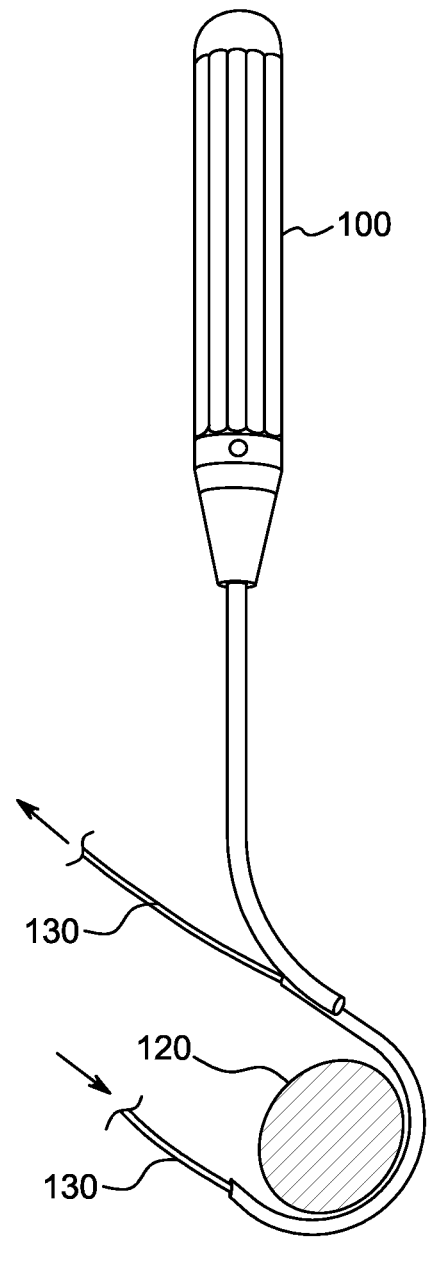

As shown in FIG. 4H, the surgeon may fully disengage the sheath 300 by extending a slit 370 therein the cable passer sheath 300 along an entire length of the cable passer sheath 300 to create an open channel 372 to remove the cable passer sheath 300 from the cable 130 and discards the cable passer sheath.

The surgeon removes the cable passer 100 from the incision.

The surgeon then secures the cable 130 around the bone 120.

Sheath Description

As shown in FIG. 2 and FIGS. 3A-3D, the cable passer sheath 300 is configured to engage the end hole of the cable passer 100. The cable passer sheath 300 includes an outer body 310 with an outer diameter 312 and having a cable passer engagement opening 322 at a cable passer engagement end 320 thereof and a cable engagement opening 332 at a cable engagement end 330 thereof. The cable passer engagement opening 322 and cable engagement opening 332 are connected by a passage 340 through the outer body 310. The passage 340 is sized and shaped to receive a cable slidably therethrough.

The inner passage 340 has a first inner diameter 342 less than the sheath outer diameter 312 and a second inner diameter 344 greater than the first inner diameter 342. The second inner diameter 344 is sized to fit around an end hole outer diameter 112 of a cable passer 100 and the first inner diameter 342 is sized to be less than the end hole outer diameter 112 and cable passer passage diameter 113. This allows the end hole end 114 of the cable passer 100 to extend into the cable passer sheath 300 but only so far due to contact between the end hole end 114 and sheath inner diameter edge 350 that extends between the first inner diameter 342 and second inner diameter 344.

As shown, the sheath inner diameter edge 350 is angled with respect to a center axis 360 of the sheath 300, which angle 362 is approximately 45 degrees. This angle 362 is configured to match an angle formed by a cable passer end hole end 114.

The first inner diameter 342 is configured to be the same or less than an inner diameter of a cable passer end hole 114, which prevents the cable 130 from being caught on any stray edges.

A slit 370 cut through the outer body 310 to the sheath 300 allows the surgeon to later extend the slit 372 and create a channel 372 through which the cable 130 may pass when removing the sheath 300. To ensure that the cable sheath 300 remains engaged during the procedure, the slit 370 extends along only a portion of a length of the outer body 310 along the cable entry end 330 of the sheath 300.

To assist in feeding the cable 130 into the sheath 300, the cable passer engagement end 320 may include a beveled edge 324. The beveled edge 324 is to assist in passing the sheath through the soft tissues since it will be passed in a cannulated fashion over the cable because the end hole 110 is not visible.

The sheath 300 itself may be of a rigid or semi-rigid sterilizable plastic known for medical properties. Without the slit, the sheath 300 may even be made from steel or other metals that can be autoclaved.

While the invention has been described with reference to the embodiments above, a person of ordinary skill in the art would understand that various changes or modifications may be made thereto without departing from the scope of the claims.

The invention claimed is:

1. A cable passer sheath configured to engage an end hole of a cable passer, the cable passer sheath comprising an outer body having an outer diameter and having a cable passer engagement opening at a cable passer engagement end thereof and a cable engagement opening at a cable engagement end thereof, wherein the cable passer engagement opening and cable engagement opening are connected by an inner passage through the outer body, wherein the inner passage has a first inner diameter less than the sheath outer diameter and a second inner diameter greater than the first inner diameter, and wherein the second inner diameter is sized to fit around an outer diameter of an end hole of a cable passer, wherein the sheath includes a center axis therethrough, wherein a sheath inner diameter edge extends between the first inner diameter and second inner diameter, wherein when viewed through a cross section, the sheath inner diameter edge on either side of the center axis is angled with respect to a single line through the sheath that is angled with respect to the center axis, wherein the single line is coincidental with the sheath inner diameter edge on both sides of the center axis;

wherein the angle is approximately 45 degrees.

2. The cable passer sheath of claim 1, wherein the first inner diameter is sized to be equal to or less than the end hole outer diameter.

3. The cable passer sheath of claim 2, wherein the first inner diameter is configured to be the same as an inner diameter of the cable passer end hole.

4. The cable passer sheath of claim 1, further comprising a slit cut through the outer body to the passage.

5. The cable passer sheath of claim 4, wherein the slit extends along only a portion of a length of the outer body.

6. The cable passer sheath of claim 1, wherein the cable passer engagement end includes a beveled edge.

7. The cable passer sheath of claim 1, wherein the sheath inner diameter edge is configured to engage the entirety of a cable passer end's beveled edge.

8. An operating equipment system including the cable passer sheath of claim 1, further comprising the cable passer.

9. The operating equipment system of claim 8, wherein the cable passer includes a beveled edge and the sheath inner diameter edge engages the entirety of the beveled edge.

* * * * *